United States Patent [19]

Avron et al.

[11] 4,115,949

[45] Sep. 26, 1978

[54] PRODUCTION OF GLYCEROL FROM ALGAE

[75] Inventors: Mordhay Avron, Rehovot; Ami Ben-Amotz, Ramat Gan, both of Israel

[73] Assignee: Yeda Research and Development Company Ltd., Rehovot, Israel

[21] Appl. No.: 800,521

[22] Filed: May 25, 1977

[30] Foreign Application Priority Data

Jun. 6, 1976 [IL] Israel .......................................... 49726

[51] Int. Cl.$^2$ ........................ A01G 7/00; A01G 33/02
[52] U.S. Cl. ............................................................. 47/1.4
[58] Field of Search ............................................... 47/1.4

[56] References Cited

U.S. PATENT DOCUMENTS

| 2,732,661 | 1/1956 | Spoehr et al. | 47/1.4 |
| 3,195,271 | 7/1965 | Golueke et al. | 47/1.4 |
| 3,650,068 | 3/1972 | Meyer et al. | 47/1.4 |

FOREIGN PATENT DOCUMENTS

| 4,516,075 | 4/1970 | Japan | 47/1.4 |
| 5,174,891 | 6/1976 | Japan | 47/1.4 |

Primary Examiner—Robert E. Bagwill
Attorney, Agent, or Firm—Browdy and Neimark

[57] ABSTRACT

A process for the production of glycerol and proteinous substances of nutritive value which comprises cultivating algae of the Dunaliella species in a nutrient medium containing the mineral requirements of growth of the algae, said nutrient medium having a sodium chloride content of at least 1.5 M, the cultivation being effected while an adequate supply of carbon dioxide is provided and continued until a maximum concentration of algae is obtained, and continuing the cultivation of the algae in a nutrient medium having a content of sodium chloride of at least 3 M, cultivating the algae in this second nutrient medium until a high glycerol content is established, harvesting the algae, recovering from same the glycerol, and recovering the residue having a high protein content.

16 Claims, 1 Drawing Figure

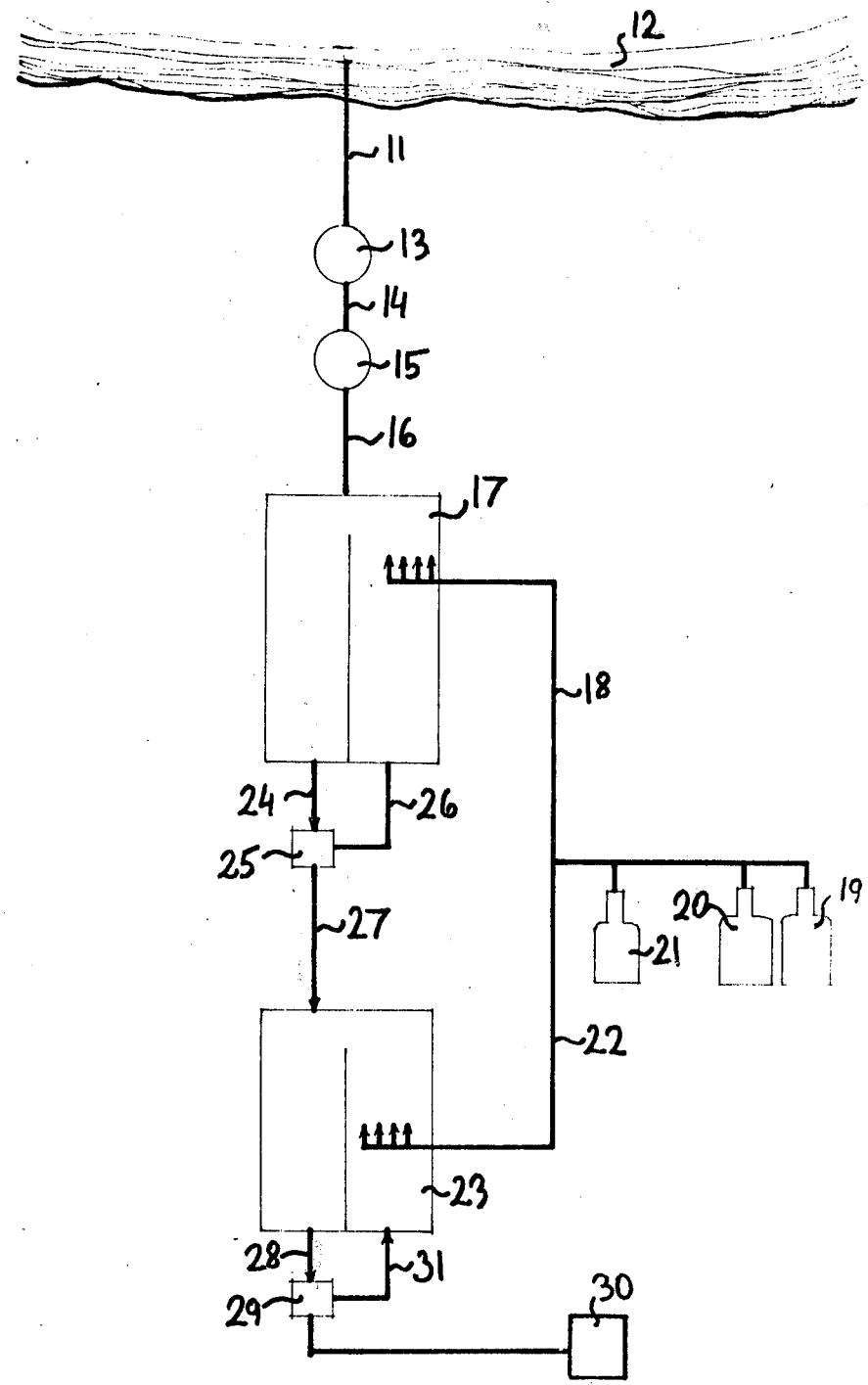

PRODUCTION OF GLYCEROL FROM ALGAE

FIELD OF THE INVENTION

The present invention relates to a novel process for the production of certain valuable organic compounds and also of nutritive products by the cultivation of halophilic algae, and especially of algae of the *Dunaliella* species.

Various algae of the *Dunaliella* species, such as *Dunaliella parva*, a green small unicellular alga ($\sim 25\ \mu^3$), *Dunaliella salina*, a green medium size unicellular alga ($\sim 100\ \mu^3$), *Dunaliella* (B), a green-red big unicellular alga ($\sim 500\ \mu^3$), *Dunaliella tertiolecta* and *Dunaliella primolecta* contain glycerol. These types of algae may accumulate under extreme conditions up to about 85 percent by weight of glycerol, and the quantity of glycerol increases with an increase of the salinity of the medium in which the algae are grown. *Dunaliella* (B) contains in addition to glycerol also a quantity of up to about 1.2 percent by weight of $\beta$-carotene. The glycerol of the algae may be separated and utilized. The residue contains a large percentage of proteins, and constitutes a valuable source of proteins which may be used for various nutritive purposes.

Various types of algae of the *Dunaliella* species which may be used in the process of the present invention are known and have been deposited in Culture Collections from which they may be obtained upon request. Amongst these there may be mentioned the following, deposited in the Culture Collection of Indiana University, Department of Botany, Bloomington, Indiana, U.S.A.: *Dunaliella peircei*, LB 295; *Dunaliella primolecta*, LB 1000; *Dunaliella salina*, LB 200, LB 1644; *Dunaliella tertiolecta*, LB 999, *Dunaliella sp*, LB 199. A detailed description of the algae of the *Dunaliella species appears in Butcher R. W. (*1959) "An Introductory Account of Smaller Algae of British Coastal Waters", I. Introduction and Chlorophyceae, Fish Inverst. Series 4.

*Dunaliella* fluorishes on salt water and requires sunlight, carbon dioxide from the air and salt water for growth. Since this algae grows best on saline water, artificial ponds can be dug in uncultivable arid areas which have an ample supply of brackish or saline water. It is possible to utilize the harvested algae as source for the production of glycerol, and the residue can be used as animal foodstuff since it has a high nutritive value. Another possible byproduct is $\beta$-carotene. *Dunaliella* is capable to convert, under controlled conditions of cultivation, water and carbon dioxide into glycerol, and this up to a high content of this valuable constituent per unit weight of the algae. As the salt concentration of the medium in which *Dunaliella* is grown is increased, up to a certain value, the content of glycerol of the algae increases, and thereby *Dunaliella* protects itself against dehydration, counterbalancing by the higher glycerol content the external salt, thus substantially reducing water loss to nearly zero. From the above it is clear that *Dunaliella* algae constitute valuable means for the direct conversion of sunlight, i.e., solar energy and carbon dioxide to valuable chemicals, and thus to chemical energy. Glycerol has different uses and can be used as energy source for numerous purposes.

STATE OF THE PRIOR ART

The role of glycerol in the osmotic regulation of the halophilic alga *Dunaliella parva* was described in Plant. Physiol (1973) 51, 875–878, and it was shown that at around 1.5 M NaCl in the medium, the glycerol content of the algae was about 2.1 M.

SUMMARY OF THE INVENTION

According to the present invention there is provided a process for the controlled cultivation of halophilic algae of the *Dunaliella* species for the production of glycerol, of algal food and $\beta$-carotene from algae thus grown. The algae are grown under controlled conditions of irradiation and aeration, on a culture medium providing an optimum of growth, thus supplying the algae optimum growth conditions. Alternate sources of carbon dioxide can be utilized instead. The algae are grown on a medium containing suitable salt concentration. Irradiation may be by means of artificial light or by sunlight. The cultivation is continued until a predetermined cell concentration per unit volume is reached, the cells or part of these are harvested, and the glycerol is separated. The residual material has a definite nutritive value and can be used as animal feedstuff or as additive to such or other feedstuffs, $\beta$-carotene can be recovered as by product.

It was found that when *Dunaliella parva* is grown in 1.5 M sodium chloride, a concentration of about 2 M of glycerol is established in the algae. When the salt concentration of the medium is increased to about 3 M, the glycerol concentration of the algae is increased to about 4M, which constitutes about 40 percent by weight of the volume of the algae. When the salt concentration of the medium is varied, the glycerol concentration corresponding to the changed concentration is established within a few hours. Under optimum conditions of cultivation there may be obtained a glycerol content of up to about 85% by weight of the dry cell weight.

When glycerol is burnt, its caloric value is about 4.3 Cal. per gram. The average solar energy per square kilometer is about $2 \times 10^9$ kilo-Cal, and since the utilization of light by photosynthesis is only 10%, it can be calculated that this species of algae is capable of producing a maximum of about 40 tons of glycerol per day per square kilometer.

Algae of this type are found in brackish water, in sea water, even in water of the Dead Sea, and in the Dead Sea area. Under natural conditions the concentration of the algae is quite low and without commercial interest. Cultivation under controlled conditions makes possible a commercial exploitation of the specific properties of this type of algae.

Optimum conditions of cultivation of algae of the *Dunaliella* species were sought, and after prolonged experiments such optimum conditions were established, under which there is obtained both a rapid rate of cultivation and also a high content of glycerol. Cultures of *Dunaliella* were maintained on agar. Cultures were also maintained and grown on liquid media comprising the following constituents:

The nutrient medium advantageously contains the following nutrients (molar content): Sodium chloride: 1 to 5 M, and preferably 1 M to 4 M; $Mg^{++}$: about 1mM to 100mM, and preferably about 5mM; $K^+$: about 1mM to 10mM, and preferably about 3mM to 6mM; $Ca^{++}$: about 0.1mM to 20mM, and preferably 0.2 to 0.4mM; Fe-EDTA: about 0.5 $\mu$M to 45 $\mu$M and preferably 1.0 to 2 $\mu$M; $SO_4^=$: about 1 to 5 mM, and preferably 4 mM to 6 mM; $NO_3^-$: about 1 mM to 20 mM, preferably about 3 to 5 mM; $PO_4^=$: about 0.01 mM to 1 mM, preferably about 0.1 mM to 0.2 mM.

Seawater medium: seawater augmented to a sodium chloride content of 1 M to 4 M NaCl, about 1 to 20 mM potassium nitrate and preferably about 3 to 5 mM potassium nitrate, about 0.01 mM to 1 mM $KH_2PO_4$ and preferably about 0.1 mM $KH_2PO_4$; about 0.5 uM to 50 uM $FeCl_3$-EDTA and preferably about 1 uM to 2 uM $FeCl_3$-EDTA. Instead of potassium nitrate about 0.5 mM to 10 mM, and preferably 2 mM to 3 mM $NH_4NO_3$ can be used; the potassium dihydrogen phosphate can be replaced by 0.1 mM to 2 mM $NH_4H_2PO_4$ or by 0.1 mM to 1mM $(NH_4)_2HPO_4$ gives satisfactory results.

Filtered sea water enriched so as to have about the above content of cations and anions is a suitable culture medium. No vitamin additives are needed. The algae were first cultivated in a 200 ml volume without agitation and under irradiation with fluorescent daylight type light at 20° C. The culture was transferred to a 2 liter volume, afterwards to 20 liter etc.; the cultivation being carried out in each stage so as to give about $2 \times 10^6$ algae per ml. The ultimate cultivation under laboratory conditions was in 300 l PVC containers with fluorescent light irradiation.

As the algae utilize carbon dioxide during the process of photosynthesis, the pH tends to increase. *Dunaliella* grows well on carbon dioxide and on bicarbonate. Various experiments have shown that the optimum rate of cultivation can be reached when air containing about 1 percent carbon dioxide was bubbled through at a rate of 1.0 liter of such air per liter of culture medium or by bubbling through 10 ml pure carbon dioxide per liter medium per hour. A concentration of about 10 to 50 mM bicarbonate can be used instead of the carbon dioxide, and when this is used the pH is adjusted to about 6 to 9, preferably around pH 8.0 by the addition of a suitable quantity of tris-buffer, of hydrochloric acid, of nitric acid, or of phosphoric acid. The bubbling through of the air agitates the culture medium and supplies the required quantity of carbon dioxide. The algae grow well at a pH between about 7 and 9. Optimum growth on a medium containing bicarbonate is at a pH of about 8.5 to 9.0. The optimum pH for growth in a medium through which carbon dioxide is bubbled is 7.0 to 8.5. The pH is advantageously adjusted with carbon dioxide, nitric acid or hydrochloric acid. $CO_2$ is the preferred agent for the adjustment of the pH.

The optimum temperature for the cultivation of *Dunaliella* is about 33° C. *Dunaliella* withstands temperatures as high as about 45° C and as low as about 4° C.

Due to the absorption of sunlight by water, the best results can be obtained outdoors with bodies of water up to 30 cm deep, as at greater depth the penetration of sunlight is not sufficient. In such bodies of water the water is advantageously agitated by bubbling through air supplying the required carbon dioxide.

Various contaminating microorganisms, such as bacteria, fungi, zooplankton, etc., can be excluded by growth at concentrations of sodium chloride exceeding about 2 M. When a heavy contamination appears, a sudden increase of sodium chloride concentration to about 3 M generally inhibits such contamination.

The optimum growth of *Dunaliella* takes place at a concentration of sodium chloride of about 1.5 M whereas maximum concentration of glycerol is attained at about 4 M NaCl. The algae are therefore preferably cultivated first at 1.5 M sodium chloride to obtain a maximum concentration of cells per unit volume and subsequently transferred to a medium of at least about 3 M and preferably about 4 M sodium chloride. *Dunaliella* increases the glycerol content to the increased level during about 8 to 10 hours and this may reach up to about 50 percent by dry weight. Both growth and glycerol accumulation are under metabolic conditions of illumination and carbon dioxide supply.

The ultimate cultivation is effected until a concentration of about $10^9$ to $10^{10}$ algae per liter is obtained, which corresponds to about 0.2 to 2.0 gram of wet algae per liter, i.e., about 0.1 volume percent. The algae are easily separated by settling out or by centrifugation at low velocities (at about 1000 g). Experiments have shown that about 30% of the daily algae growth settles out on the bottom of the culture tank.

Cultures can be harvested by continuous centrifugation in a batch-centrifuge or in a "de-sludger" centrifuge at about 3000 g. Generally it is advantageous to harvest each day about half the cells, the remaining culture being diluted with fresh medium. One liter containing about $10^7$ Dunaliella cells per milliliter yields about 1 gram fresh algal paste per day, i.e., about 0.5 g dry weight.

Algae can be harvested by gravitational sedimentation. The culture is transferred to a conical tank where they settle out. About 30 percent of the daily growth settles out by gravitation and there a concentration factor of about 25 is attained. Centrifugation of this sediment yields fresh algal paste.

The algae may be flocculated from the culture medium by the addition of certain salts, such as ferric chloride, aluminum chloride or aluminum sulfate. A concentration of about 0.1 mM to 0.5 mM ferric chloride, or about 0.1 to 0.5 mM aluminum chloride or about 0.1 mM to 0.5 mM aluminum sulfate results in the flocculation of *Dunaliella* and the settled out cells may be harvested after about one hour. The sediment is centrifuged to yield algal paste.

The algae can be concentrated by cross-flow filtration through a cross-flow filtration system of the type supplied by A. T. Ramot Plastics Ltd., Tel-Aviv, which comprises a plurality of porous plastic tubings assembled in a modular filtration unit containing bundles of many tubes. About 75 liters of algae culture can be concentrated per hour yielding a concentration by a factor of 15. Centrifugation yields algal paste.

After centrifugation or collection of the algae by other means, there is obtained a paste which contains about 50 percent by weight of water. The dry algae contain at optimum conditions about 85 percent by weight of glycerol (maximum), and generally about 50 percent by weight. Glycerol has a boiling point of about 280° C at atmospheric pressure; under a pressure of about 0.1 mm Hg the boiling point is about 130° C. It is evident that the glycerol may be distilled off, but this has a detrimental effect on the proteinaceous residue which has a high nutritive value. When *Dunaliella* is transferred into a medium containing less than 0.5 M salt, all the glycerol passes into the surrounding medium. It ought to be stressed that *Dunaliella* has no cellulose-cell wall.

BRIEF DESCRIPTION OF THE DRAWING

A cultivation plant for the cultivation of *Dunaliella* algae under conditions resulting in optimum recoveries of the desired products is described with reference to the enclosed schematical diagramical drawing, not according to scale.

DESCRIPTION OF THE PREFERRED EMBODIMENT:

According to one of the preferred embodiments of the present invention, harvested *Dunaliella* is introduced into a medium of less than 0.5 M salt, and preferably of about 0.25 M sodium chloride, the glycerol passes into this medium, the cell debris is separated by centrifugation or other means, and the glycerol is recovered from the saline medium by distillation under vacuum.

EXTRACTION AND DISTILLATION OF GLYCEROL

Glycerol can be distilled from fresh algal paste by fractional vacuum distillation. This has a certain detrimental effect on the residual proteinaceous material.

Glycerol can be extracted in water. 10 g fresh *Dunaliella* paste are suspended in 50 ml water and stirred at room temperature during 10 minutes and centrifuged at 3000 g for 30 minutes. The sediment is dried at 80° C during 1 hour and glycerol is distilled from the supernatant by fractional vacuum distillation.

Glycerol can be extracted by ethanol: 10 g of *Dunaliella* paste is suspended in 10 to 20 ml technical ethanol, stirred at room temperature during 20 minutes, press-filtered or centrifuged at 500 g for 5 minutes. The sediment is dried at 50°–60° C for 1 hour or under sunlight for a few hours. The supernatant contains about 2.5 g glycerol and traces of chlorophyll. The proteinous residue contains $\beta$-carotene.

The glycerol can be recovered from the supernatant by fractional vacuum distillation. First, ethanol is removed around 20° C under aspirator vacuum (about 20 mm Hg); after this chlorophyll is extracted by mixing (1:1 by volume) with trichloroethylene and phase separation. In the third step 0.1% alum and 0.2% ferric chloride are added to the glycerol-water mixture to precipitate residues of proteins and the mixture is pressure-filtered through filter paper. Water is removed at about 32° C under aspirator vacuum and after this glycerol is distilled off at 130° C under a vacuum of about 0.1 mm Hg.

The proteinous residue is extracted by means of cyclohexane (1:1 by volume) and the solid is pressure-filtered. The cyclohexane is removed from the liquid by vacuum evaporation and the residue is washed with ethanol to remove chlorophyll, leaving a residue of substantially pure $\beta$-carotene.

Various experiments have shown that *Dunaliella* multiplies in a manner doubling the population each day. Thus, from a tank of 30 cm depth, there may be harvested from each square meter about 0.3 Kg algae when half the algae are harvested each day, which corresponds to about 0.15 Kg per day. Extrapolation to large scale cultivation shows that from each square kilometer there may be expected a daily harvest of about 75 tons per day, which corresponds to about 40 tons glycerol. As by-product a quantity of about 40 tons dry proteinaceous material may be expected daily.

The invention is illustrated by way of example with reference to the following large scale laboratory experiments and results of field trials. The examples are by way of illustration only and ought to be construed in a nonlimitative manner.

Algae: *Dunaliella salina, Dunaliella parva,* and other *Dunaliella* species

Medium: Sea water filtered through 25 $\mu$ and 5 $\mu$ Filters and enriched with the following additives: NaCl up to 1.5 M; 2 mM $KNO_3$; 0.2 mM $KH_2PO_4$ Large scale culture: *Dunaliella* was grown in above medium in glass bottles with artificial fluorescent light of 200 f.c., 25° C and occasional shaking. 20 liters of culture containing $2 \times 10^6$ cells per ml were transferred to 2 clear PVC drums containing 600 liters of above medium. Each PVC drum was covered with a tight fitting lid through which several sleeves containing fluorescent lamps and stainless steel tubing for cooling were inserted.

Aeration and mixing were by bubbling about 0.4 liters per liter medium per hour of air enriched with 1-2% $CO_2$ through air bubblers and/or porous plastic tubing. Porous polyethylene tubing can be used for the controlled supply of carbon dioxide and for simultaneous agitation. Porous tubing having a wall thickness of about 1 mm and internal diameter of about 6 mm, average porosity 50%, average pore size about 12 um, was used to bubble 1% carbon dioxide into the culture medium at a flow rate of 1 liter per hour per liter medium. Under these conditions *Dunaliella* grows at a growth rate of 1 to 2 divisions per day and is harvested at concentrations of about $5 \times 10^6$ cells per milliliter. An alternative method of mixing is downflow of the culture in a canal of about 1 meter width at a continuous flow rate of up to 30 cm/sec. An "air-lift" creates the required difference in height and permits culture flow. Carbon dioxide is introduced at a controlled rate along a few locations of the canal.

Illumination was both with external and internal "cool white" fluorescent lamps, 10 per drum.

A spiral of stainless steel tubing was placed within the drum for circulation of cold water. Temperature was maintained at 24° C $\pm$ 1° C.

*Dunaliella* grew at a rate of 1-2 divisions per day and were harvested at concentrations of around $5 \times 10^6$ cells per ml. 10 mM bicarbonate can replace $CO_2$ in air as a carbon source. In the latter case pH was controlled around 8.0 by bubbling air containing 2% $CO_2$. Harvest: Cultures were harvested by continuous centrifugation in a Sharples model LE Bench-Scale centrifuge or in a dairy cream-separator Alfa Laval No. 16 at a centrifugal force of $1000 \times g$ with a flow rate of 150 liters per hour.

About half of the culture was harvested each day, with the remaining culture diluted accordingly with fresh medium. 300 liters containing $5 \times 10^6$ *Dunaliella* cells per ml. yielded 300 gr fresh algal paste per day. Preparation of dried cells: 300 gr of fresh *Dunaliella* paste were suspended in 1.5 liters of deionized water, mixed at room temperature for 10 minutes and centrifuged in a Sorvall centrifuge at $3000 \times g$ for 30 minutes. The pellet was dried by liophilization (6 grams).

The dried material can be used as food. The supernatant contains the glycerol. Distillation of glycerol: Glycerol was distilled from the supernatant by a fractional vacuum distillation. In the first step water was removed around 32° C under aspirator vacuum (about 20 mm Hg). In the second step glycerol was distilled at about 130° C with vacuum by an oil vacuum pump (about 0.01 mm Hg). 40 gr of glycerol were obtained from 300 gr fresh algal paste under the indicated growth conditions. Increasing the external salt concentration in the medium should result in an accumulation of more glycerol in the cells up to 100 gr glycerol per 300 gr fresh algal weight.

As illustrated in the enclosed Drawing, a cultivation plant comprises a conduit 11 leading from the source of seawater 12 (if such is used as primary source of the nutrient medium), via water softener 13, conduit 14, reservoir of softened water 15 and conduit 16 into the first cultivation pond 17 of about 100 m² area, wherein *Dunaliella* algae are grown at a salt concentration of about 12 percent sodium chloride, in a culture medium containing the other nutrients defined in the specification at their optimum concentration, these nutrients as well as carbon dioxide or bicarbonate solution being supplied to this pond 17 via conduit 18 from supply vessels of liquid solutions 19 and 20, and from the source of gaseous carbon dioxide 21, which can also designate a supply vessel of a solution of a suitable bicarbonate, respectively. The supply vessels 19, 20 and 21 supply nutrients via conduit 22 to the second cultivation pond 23. Pond 17 is connected with pond 23 via conduits 24, through the device 25 which serves to pump *Dunaliella* from pond 17 to pond 23, of about equal area, part of the nutrient medium being returned via conduit 26 to pond 17, while part of the culture is pumped via conduit 27 to pond 23, the culture medium containing about 1 percent by weight of *Dunaliella*. In pond 23 a sodium chloride concentration of about 24 percent is maintained, and this results in a high glycerol content of the *Dunaliella*. These are pumped via conduit 28 to the separator 29 and via conduit 30 to a reservoir of the product, which is an algae paste of about 50 percent water content. Part of the nutrient liquid is returned to pond 23 via conduit 31. The combinatiOn of two ponds wherein different concentrations of salt are maintained results in high yields of *Dunaliella* of high glycerol content: in the first pond conditions are maintained for an optimum growth rate, whereas in the second pond the high salt (sodium chloride) content of the nutrient medium results in a very high glycerol content of the harvested algae and thus in a high yield of glycerol.

We claim:

1. A process for the production of glycerol and proteinous substances of nutritive value which comprises cultivating algae species of the *Dunaliella* genus in a nutrient medium containing the mineral requirements of growth of the algae, said nutrient medium having a sodium chloride content of at least 1.5 M, the cultivation being effected while an adequate supply of carbon dioxide is provided and continued until a maximum concentration of algae is obtained, and continuing the cultivation of the algae in a nutrient medium having a content of sodium chloride of at least 3 M, cultivating the algae in this second nutrient medium until a high glycerol content is established, harvesting the algae, recovering from same the glycerol, and recovering the residue having a high protein content.

2. A process according to claim 1, wherein the *Dunaliella* used for cultivation is *Dunaliella salina, Dunaliella* (b), *Dunaliella primolecta, Dunaliella tertiolecta,* or *Dunaliella peircei.*

3. A process according to claim 1, wherein the carbon dioxide is supplied in gaseous form.

4. A process according to claim 1, wherein the carbon dioxide is supplied in the form of bicarbonate.

5. A process according to claim 1, wherein part of the algae are allowed to settle out, and these are harvested.

6. A process according to claim 1, wherein the algae are preconcentrated in a filter unit.

7. A process according to claim 1, wherein the algae are harvested by centrifugation.

8. A process according to claim 1, wherein the algae are grown in an outdoor body of water of about 15 to 30 cm depth.

9. A process according to claim 1 wherein the nutrient medium contains 1 mM to 10 mM $Mg^{++}$, 1 mM to 10 mM $K^+$, 0.1 mM to 20 mM $Ca^{++}$, Fe-EDTA about 0.5 $\mu$m to 45 $\mu$m, $SO_4^=$ about 1 mM to 5 mM; and $NO_3$ about 1 mM to 20 mM; $PO_4^=$ about 0.01 mM to 1 mM.

10. A process according to claim 1, wherein the nutrient medium is sea-water augmented to a suitable sodium-chloride and mineral content.

11. A process according to claim 1, wherein the alga is *Dunaliella* (B) and an additional product is $\beta$-carotene.

12. A process according to claim 2, wherein contaminating micro-organisms are eliminated by raising the sodium chloride content above 2 M.

13. A process according to claim 2, wherein algae are precipitated by addition of ferric chloride, aluminum chloride or aluminum sulfate.

14. A process according tO claim 2, wherein the harvested algae are suspended in water resulting in a release of the glycerol and separating the glycerol from the proteinous residue.

15. A process according to claim 2, wherein the glycerol is recovered by fractional distillation.

16. A process according to claim 2, wherein the algae are extracted with ethanol, the extract is separated from the proteinous residue and glycerol is recovered from the ethanol extract by fractional distillation.

* * * * *